United States Patent [19]

Soper

[11] 4,192,670

[45] Mar. 11, 1980

[54] ACETAL DERIVATIVES OF 4-(SUBSTITUTED AMINO)-3,5-DINITROBENZALDEHYDES

[75] Inventor: Quentin F. Soper, Indianapolis, Ind.

[73] Assignee: Eli Lilly and Company, Indianapolis, Ind.

[21] Appl. No.: 821,280

[22] Filed: Aug. 3, 1977

Related U.S. Application Data

[60] Division of Ser. No. 707,416, Jul. 21, 1976, Pat. No. 4,054,439, which is a division of Ser. No. 557,866, Mar. 12, 1975, abandoned, which is a continuation-in-part of Ser. No. 514,674, Oct. 15, 1974, abandoned.

[51] Int. Cl.$^2$ ............................................. A01N 9/20
[52] U.S. Cl. ..................... 71/121; 260/573; 260/574; 71/88; 71/94; 71/95; 71/105
[58] Field of Search .................. 260/573, 574; 71/121, 71/124

[56] References Cited

U.S. PATENT DOCUMENTS

| | | | |
|---|---|---|---|
| 2,553,555 | 5/1951 | Drake | 71/124 |
| 3,257,190 | 6/1966 | Soper | 260/574 |
| 3,585,242 | 6/1971 | Roos et al. | 71/124 |
| 3,672,866 | 6/1972 | Damiano | 71/121 |
| 3,764,624 | 10/1973 | Strong et al. | 71/121 |
| 3,890,134 | 6/1975 | Teach | 71/118 |
| 4,046,758 | 9/1977 | Woods et al. | 260/573 |

FOREIGN PATENT DOCUMENTS 2361463  6/1974  Fed. Rep. of Germany ............ 71/121

*Primary Examiner*—Glennon H. Hollrah
*Attorney, Agent, or Firm*—Dwight E. Morrison; Everet F. Smith

[57] ABSTRACT

Novel compounds identified as acetal derivatives of 4-(substituted amino)-3,5-dinitrobenzaldehydes, effective as herbicides, and intermediates for their preparation.

9 Claims, No Drawings

ACETAL DERIVATIVES OF 4-(SUBSTITUTED AMINO)-3,5-DINITROBENZALDEHYDES

This application is a division of application Ser. No. 707,416, filed July 21, 1976, now U.S. Pat. No. 4,054,439, which was a division of application Ser. No. 557,866, filed Mar. 12, 1975, now abandoned, which was a continuation-in-part of application Ser. No. 514,674, filed Oct. 15, 1974, now abandoned.

BACKGROUND OF THE INVENTION

1. Field of the Invention

Ever since the invention of 2,4-dichlorophenoxyacetic acid and its utility as a herbicide, the study of organic chemical herbicides has been underway. The study has produced many and varied organic chemical herbicides which have become increasingly sophisticated in their action.

2. Description of the Prior Art

In the prior art, Soper, U.S. Pat. No. 3,257,190 (June 21, 1966), teaches the use of N,N-disubstituted-2,6-dinitroanilines in novel processes for selectively eliminating germinating and seedling weed grasses and broadleaf weeds.

Also in the prior art, McQueen, et al., U.S. Pat. No. 2,481,434 (Sept. 6, 1949), teach cyclic aminobenzaldehydeacetals of 1,2- and 1,3-glycols and their preparation, which compounds are alleged to be useful in the preparation of polymeric color formers. There is no suggestion that these compounds of McQueen et al., or related compounds, possess herbicidal activity.

SUMMARY

There are now disclosed novel compounds having herbicidal activity, identified as acetals of 4-(substituted amino)-3,5-dinitrobenzaldehydes, and novel intermediates for their preparation.

DESCRIPTION OF THE PREFERRED EMBODIMENT

This invention relates to novel compounds identified as acetals of 4-(substituted amino)-3,5-dinitrobenzaldehydes. The novel compounds have the formula

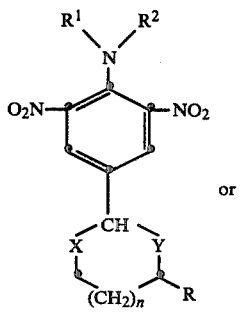

(I)

or

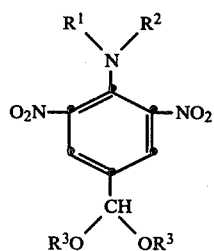

(II)

wherein

X and Y are the same or different and are oxygen or sulfur;

R is hydrogen or methyl;

$R^1$ represents
(A) $C_1$-$C_6$ alkyl, optionally monosubstituted with
(1) methoxy,
(2) cyano, or
(3) halo,
(B) $C_3$-$C_4$ alkenyl,
(C) halo($C_3$-$C_4$)alkenyl,
(D) $C_3$-$C_4$ alkynyl,
(E) cyclopropylmethyl, or
(F) tetrahydrofurfuryl;

$R^2$ represents
(A) $C_1$-$C_6$ alkyl, optionally monosubstituted with
(1) methoxy,
(2) cyano, or
(3) halo,
(B) $C_3$-$C_4$ alkenyl,
(C) halo($C_3$-$C_4$)alkenyl,
(D) $C_3$-$C_4$ alkynyl,
(E) cyclopropylmethyl,
(F) tetrahydrofurfuryl, or
(G) hydrogen;

provided that $R^1$ and $R^2$ together contain no more than 8 carbon atoms; or $R^1$ and $R^2$, taken together with the nitrogen atom to which they are attached, form
(A) piperidino,
(B) pyrrolidino,
(C) morpholino,
(D) aziridino,
(E) azetidino, or
(F) hexahydroazepino;

$R^3$ is $C_1$-$C_3$ alkyl; and n is 0 or 1.

This invention also relates to novel compounds useful as intermediates in the preparation of compounds of the formulas (I) and (II) above, said intermediate compounds being of the formula

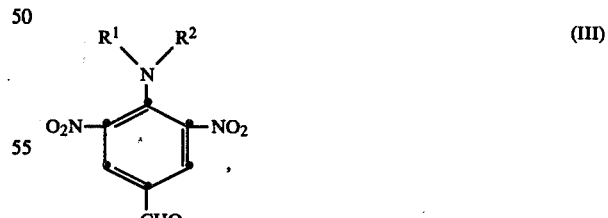

(III)

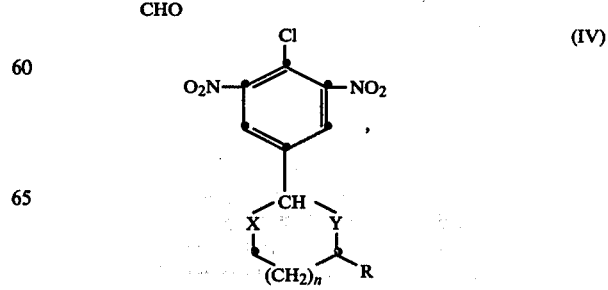

(IV)

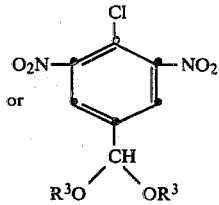

wherein X, Y, R, $R^1$, $R^2$, and $R^3$ have the same meaning as set forth hereinbefore.

In the generic formulae, $C_1$–$C_6$ alkyl, $C_3$–$C_4$ alkenyl, and $C_3$–$C_4$ alkynyl refer to groups including methyl, ethyl, propyl, sec.-butyl, hexyl, isopropyl, n-pentyl, t-butyl, allyl, methallyl, crotyl, propargyl, and 2-butynyl.

Halo means bromo, chloro, fluoro, or iodo.

Halo($C_3$–$C_4$)alkenyl refers to chloroallyl, bromoallyl, 4-chloro-2-butenyl, 4-bromo-1-butenyl, 4-fluoro-2-butenyl, iodoallyl, and the like.

Novel compounds coming within the scope of the generic formulae (I) and (II), above, include, but are not limited to, the following:

4-(1,3-Dioxolan-2-yl)-N,N-diethyl-2,6-dinitroaniline,
N,N-Dibutyl-4-(1,3-dioxolan-2-yl)-2,6-dinitroaniline,
4-(1,3-Dioxolan-2-yl)-N-ethyl-N-methyl-2,6-dinitroaniline,
N,N-Diethyl-4-(4-methyl-1,3-dioxolan-2-yl)-2,6-dinitroaniline
N,N-Dibutyl-4-(4-methyl-1,3-dioxolan-2-yl)-2,6-dinitroaniline,
4-(4-Methyl-1,3-dioxolan-2-yl)-2,6-dinitro-N-ethyl-N-propylaniline,
4-(1,3-Dioxan-2-yl)-N,N-diethyl-2,6-dinitroaniline,
4-(1,3-Dioxan-2-yl)-N-ethyl-2,6-dinitro-N-propylaniline,
N,N-Diethyl-2,6-dinitro-4-(1,3-oxathiolan-2-yl)-aniline,
N,N-Dibutyl-2,6-dinitro-4-(1,3-oxathiolan-2-yl)-aniline,
4-(1,3-Dithiolan-2-yl)-N,N-diethyl-2,6-dinitroaniline,
4-(1,3-Dithiolan-2-yl)-N-ethyl-2,6-dinitro-N-propylaniline,
N,N-Dibutyl-4-(m-dithian-2-yl)-2,6-dinitroaniline,
4-(m-Dithian-2-yl)-N,N-diethyl-2,6-dinitroaniline,
2,6-Dinitro-N,N-(3-oxapentamethylene)-4-(1,3-oxathiolan-2-yl)aniline,
N-Butyl-4-(m-dithian-2-yl)-2,6-dinitro-N-propylaniline,
4-(1,3-Dioxolan-2-yl)-N,N-hexamethylene-2,6-dinitroaniline,
4-(1,3-Dioxolan-2-yl)-2,6-dinitro-N,N-(pentamethylene)aniline,
4-(4-Methyl-1,3-dioxolan-2-yl)-N,N-dimethylene-2,6-dinitroaniline,
N,N-Dibutyl-4-(1,3-dioxan-2-yl)-2,6-dinitroaniline,
4-(1,3-Dioxan-2-yl)-2,6-dinitro-N,N-(trimethylene)-aniline,
2,6-Dinitro-α,α-dipropoxy-N,N-dipropyl-p-toluidine,
α,α-Diethoxy-2,6-dinitro-N,N-(tetramethylene)-p-toluidine, and the like.

Novel compounds useful as intermediates and coming within the scope of the generic formulae (III), (IV), and (V), above, include, but are not limited to the following:
3,5-Dinitro-4-(dipropylamino)benzaldehyde
3,5-Dinitro-4-(diethylamino)benzaldehyde
3,5-Dinitro-4-(dibutylamino)benzaldehyde
3,5-Dinitro-4-N-ethyl-N-methylaminobenzaldehyde
4-(1,3-Dithiolan-2-yl)-2,6-dinitrochlorobenzene
4-(1,3-Dioxolan-2-yl)-2,6-dinitrochlorobenzene
4-(4-Methyl-1,3-dioxolan-2-yl)-2,6-dinitrochlorobenzene
4-(m-Dithian-2-yl)-2,6-dinitrobromobenzene
α,α-Diethoxy-2,6-dinitrochloro-p-toluene
α,α-Dimethoxy-2,6-dinitrobromo-p-toluene In addition to its utility as an intermediate, one of the above compounds, identified as 3,5-dinitro-4-(dipropylamino)benzaldehyde, is active as an herbicide when applied at the rate of about 8 pounds per acre.

The novel compounds coming within the scope of generic formulae (I) and (II), together with novel compounds of generic formula (III), have been found useful as preemergent herbicides for the treatment of a soil area or locus infested with weed grass seeds and broadleaf weed seeds, for instance, in an area to be planted to corn, soybeans, or cotton. The herbicidally active compounds are applied in the form of a spray, a dust, or a granular formulation. The herbicidally active compounds are applied by methods well known to the art onto the area at the rate of from about ½ to about 32 pounds per acre. For field applications, I prefer to spray or dust the herbicidal compositions containing the novel compounds of this invention at the rate of about 1 to about 16 pounds of active ingredient per acre. If, however, the herbicidal compositions are spread in a granular form over the area to be treated, I prefer to employ a greater amount of active material per acre, suitably in the range of about 8 to about 16 pounds per acre.

These compounds can also be used in the control of weed grass seeds in miscellaneous places such as gravel driveways, clay tennis courts, walks, road shoulders, and the like, where the elimination of seedling grasses is desired. Compositions containing the novel herbicidally-active compounds are sprayed, dusted, or spread by other methods well known to the art onto the particular locus at the rate of around 2 to 32 pounds per acre or somewhat more if necessary; for example, 50 pounds active ingredient per acre.

The novel compounds act as preemergent herbicides and kill undesirable grasses such as the crabgrasses (*Digitaria sanguinalis* and *Digitaria ischaemum*); green and yellow foxtails (*Setaria viridis* and *Setaria lutescens*); and broadleaf weeds such as pigweed (*Amaranthus retroflexus*). In addition, the compounds are active as preemergent herbicides against velvetleaf (*Abutilon theophrasti*), and, at the higher level of treatment, against Pennsylvania smartweed, (*Polygonum pensylvanicum*).

The compounds are formulated for use as preemergent selective herbicides either as dusts, spray concentrates, spreadable granules, or wettable powders. The compounds are quite insoluble in water and for the preparation of emulsion-type sprays or wettable powders, the compounds desirably are formulated with a wetting agent or surfactant. The wetting agent or surfactant used in formulating the emulsion-type sprays or wettable powders can be illustratively polyoxyethylene sorbitan monooleate, polyglycol ether sulfonates, alkylamine dodecylbenzenesulfonate, and the like. In the preparation of spreadable granules, the inert diluent used can be calcined attapulgite clay. Dispersions can be prepared on herbicidally inert carriers such as vermiculite, peat moss and the like.

The novel compounds of this invention, including the intermediate compounds as well, are readily prepared by those skilled in the art.

Preparation of the starting materials for the novel compounds begins with the synthesis of 4-hydroxy-3,5-dinitrobenzaldehyde from commercially available 4-hydroxybenzaldehyde.

Following the procedure of Paal, *Berichte* 28, 2407-2414 (1895), 4-hydroxy-3-nitrobenzaldehyde, having a melting point of about 141°-143° C., is prepared.

This 4-hydroxy-3-nitrobenzaldehyde is used to prepare 4-hydroxy-3,5-dinitrobenzaldehyde, according to the procedure of Borrows et al., *J. Chem. Soc.* S190-S199 (1949).

The above prepared 4-hydroxy-3,5-dinitrobenzaldehyde is used to prepare 4-chloro-3,5-dinitrobenzaldehyde, according to the following procedure. To a suspension of 4-hydroxy-3,5-dinitrobenzaldehyde in phosphorus oxychloride, diethylaniline is added at a slow rate. Other suitable chlorinating agents include thionyl chloride and oxalyl chloride. When addition of the diethylaniline is complete, most of the excess phosphorus oxychloride is removed from the mixture in vacuo on a steam bath, to leave a residue. The residue is then poured into a mixture of ice and water. A yellow-brown solid is formed which is filtered off and pressed dry on the filter. This solid is dissolved in a suitable solvent, such as benzene, and is chromatographed over a silica gel column, the elution also being carried out with benzene. The eluate obtained is evaporated in vacuo, leaving a solid residue. The residue is recrystallized from a mixture of ethanol and water to yield product having a melting point of about 102°-104° C., and identified as 4-chloro-3,5-dinitrobenzaldehyde. This product is used without further purification in the preparation of 3,5-dinitro-4-(substituted amino)benzaldehydes, according to the following procedure.

A solution of 4-chloro-3,5-dinitrobenzaldehyde in benzene is prepared by heating the mixture, and to the solution is added an appropriate dialkylamine, for example, dipropylamine. Other suitable solvents include toluene and xylene. The mixture immediately turns dark red-orange and forms a gel. The reaction product mixture is worked up to yield product having a melting point of about 103°-106° C., and identified as 3,5-dinitro-4-(dipropylamino)benzaldehyde. This novel compound is useful as an intermediate in the preparation of other compounds of this invention, and as mentioned above, also is active as an herbicide when applied at the rate of about 8 pounds per acre.

The novel compounds of formulae (I) or (II), supra, can be prepared by allowing a lower alkanol, such as methanol, ethanol, a 1,2- or 1,3-alkanediol, or 1,2- or 1,3-alkanedithiol, or 2-mercaptoethanol, to react with a 3,5-dinitro-4-(substituted amino)benzaldehyde in the presence of a small amount of p-toluenesulfonic acid in a suitable water-immiscible solvent. The mixture is stirred and refluxed for a period of time sufficient to complete the reaction. Such period of time is suitably about one to about four hours, depending upon the reactants. Suitable 1,2- or 1,3-alkanediols include 1,2-dihydroxyethane, 1,2-propanediol, 1,3-propanediol, and the like. Suitable 1,2-, or 1,3-alkanedithiols include 1,2-ethanedithiol, 1,2-propanedithiol, 1,3-propanedithiol, and the like. An apparatus designed to collect the water evolved during the reaction, namely, a Dean-Stark trap, is used to keep the evolved water separate from the refluxing reaction mixture. Suitable water-immiscible solvents include benzene, toluene and the like.

The reaction can be illustrated in the following manner. A mixture of 3,5-dinitro-4-(dipropylamino)benzaldehyde, 1,2-dihydroxyethane, benzene, and a small amount of p-toluenesulfonic acid is stirred and refluxed for about one hour and a Dean-Stark trap is used to collect the water evolved in the reaction. At the end of the reaction period, the reaction product mixture is poured into aqueous sodium bicarbonate solution. The aqueous layer is separated and discarded and the organic layer is evaporated in vacuo to leave an oily residue. This oily residue is identified by infrared and NMR spectra as 4-(1,3-dioxolan-2-yl)-2,6-dinitro-N,N-dipropylaniline.

The novel compounds can also be prepared by an alternate method in which the acetal derivative of the benzaldehyde is prepared as the intermediate compound, and then the amino moiety is attached to the benzene ring. Thus, 4-chloro-3,5-dinitrobenzaldehyde is allowed to react with methanol, ethanol, a 1,2- or 1,3-alkanediol, a 1,2- or 1,3-alkanedithiol, or 2-mercaptoethanol, in the presence of a small amount of p-toluenesulfonic acid in a suitable water-immiscible solvent, under the conditions set forth in the immediately preceding paragraph. Thus for example when a mixture of 4-chloro-3,5-dinitrobenzaldehyde, 1,2-ethanedithiol, benzene, and a small amount of p-toluenesulfonic acid is stirred and refluxed for a period of time sufficient to complete the reaction, that is, about 1.5 hours, and the water of reaction collected, there is obtained, after the usual work-up, 4-(1,3-dithiolan-2-yl)-2,6-dinitrochlorobenzene. This intermediate compound is then allowed to react with a suitable amine, such as dipropylamine, in a suitable solvent, such as benzene, at reflux temperature for about 15-18 hours. The reaction product mixture is then cooled, extracted with water, and the benzene layer separated and dried. The benzene layer is filtered off from the drying agent and passed through a little aluminum oxide and concentrated to dryness. The residue is recrystallized from ethanol to yield product identified as 4-(1,3-dithiolan-2-yl)-2,6-dinitro-N,N-dipropylaniline.

The intermediate compounds useful for preparing the novel compounds of this invention are synthesized according to the methods set forth in the Preparations which follow.

PREPARATION 1

4-Hydroxy-3,5-dinitrobenzaldehyde

This intermediate compound was prepared stepwise. Following the procedure of Paal, Ber. 28, 2407-2414 (1895), 4-hydroxy-3-nitrobenzaldehyde was synthesized first.

A solution of 10 g. of 4-hydroxybenzaldehyde, 40 ml. of acetic acid, and 8.8 g. of nitric acid (d.=1.4) was prepared at room temperature. This solution was heated very slowly to about 32° C., at which temperature the reaction became exothermic and an ice bath was placed around the reaction flask to control the reaction. The temperature of the reaction mixture rose quickly to about 75° C. and then dropped. A yellow solid separated. The reaction product mixture was cooled to about room temperature, then heated for a few minutes to about 35° C., and finally cooled in an ice bath. The reaction product mixture was filtered and the solid which was collected on the filter was washed three times with water. The solid was air-dried. It had a melting point of about 141°-143° C., and was identified as 4-hydroxy-3-nitrobenzaldehyde.

The 4-hydroxy-3-nitrobenzaldehyde synthesized above was then used to prepare 4-hydroxy-3,5-dinitrobenzaldehyde, following the procedure of Borrows et al., *J. Chem. Soc.* S190–S199 (1949).

A solution of 10 g. of 4-hydroxy-3-nitrobenzaldehyde in 40 ml. of concentrated sulfuric acid was prepared and cooled to about 5° C. by means of an ice bath. To the solution was added dropwise 6 g. of concentrated nitric acid (d.=1.4), while keeping the temperature of the solution below 10° C. After addition of the nitric acid was complete, the reaction product mixture was stirred for about 0.5 hours in the ice bath. The reaction product mixture was poured over ice, the resulting mixture filtered, and the solid on the filter pressed dry. The solid was recrystallized from glacial acetic acid to yield product having a melting point of about 101°–107° C., and weighing about 9 g. The product was identified by NMR spectrum as 4-hydroxy-3,5-dinitrobenzaldehyde.

PREPARATION 2

4-Chloro-3,5-dinitrobenzaldehyde

A suspension of 120 g. of 4-hydroxy-3,5-dinitrobenzaldehyde in 300 ml. of phosphorus oxychloride was prepared, and about 150 ml. of diethylaniline was added slowly to the suspension. When addition of the diethylaniline was complete, most of the phosphorus oxychloride was removed in vacuo on a steam bath, leaving a residue. The residue was poured into a mixture of ice and water. A yellow-brown solid precipitated. The solid was filtered off and pressed dry on the filter. The solid was dissolved in benzene and chromatographed over a silica gel column, eluting with benzene. The eluate was evaporated to dryness in vacuo. The residue thus obtained was recrystallized from a mixture of ethanol and water to yield a light brown material having a melting point of about 102°–104° C., and identified as 4-chloro-3,5-dinitrobenzaldehyde. It was used without further purification.

PREPARATION 3

3,5-Dinitro-4-(dipropylamino)benzaldehyde

A solution of 150 g. of 4-chloro-3,5-dinitrobenzaldehyde in 1 l. of benzene was prepared by heating, and 300 ml. of dipropylamine was added to the solution. The mixture immediately turned dark red-orange and formed a gel. The mixture was then refluxed for about 2.5 hours. The reaction product mixture was worked up by adding about 300 ml. of ether, followed by successive washings with water, dilute aqueous hydrochloric acid, and water. The ether-benzene solution was dried over anhydrous magnesium sulfate. The drying agent was filtered off and the solution evaporated to dryness in vacuo. The residue was dissolved in benzene and chromatographed on a florisil column, eluting with benzene. The fractions were collected, combined, and the solvent evaporated in vacuo. The residue was recrystallized from a mixture of ethanol and water to yield product having a melting point of about 103°–106° C. The product which was identified as 3,5-dinitro-4-(dipropylamino)benzaldehyde, weighed about 172 g.

PREPARATION 4

4-(1,3-Dioxan-2-yl)-2,6-dinitrochlorobenzene

A mixture of 5.0 g. of 4-chloro-3,5-dinitrobenzaldehyde, 2.0 ml. of 1,3-propanediol, and a small amount of p-toluenesulfonic acid, in 100 ml. of benzene was refluxed for about 3 hours, using a Dean-Stark trap to collect the evolved water of reaction. The reaction was cooled and the reaction product mixture was extracted with saturated aqueous sodium bicarbonate solution, then with brine, and the organic layer dried. The drying agent was filtered off. The dried organic layer was evaporated to dryness and the residue was recrystallized from a mixture of benzene and petroleum ether to yield product having a melting point of about 90°–92° C. The product was identified as 4-(1,3-dioxan-2-yl)-2,6-dinitrochlorobenzene.

PREPARATION 5

4-(1,3-Dithiolan-2-yl)-2,6-dinitrochlorobenzene

A mixture of 3.0 g. of 4-chloro-3,5-dinitrobenzaldehyde, 2.0 ml. of 1,2-ethanedithiol, and a small amount of p-toluenesulfonic acid, in 100 ml. of benzene was refluxed for about 1.5 hours, using a Dean-Stark trap to collect the evolved water of reaction. The reaction mixture was cooled and the reaction product mixture was extracted with saturated aqueous sodium bicarbonate solution, then with water, and the organic layer was dried. The drying agent was filtered off and the solvent was evaporated to leave a residue. The residue was recrystallized from petroleum ether to yield product having a melting point of about 105°–108° C., and identified as 4-(1,3-dithiolan-2-yl)-2,6-dinitrochlorobenzene.

The compounds prepared as described hereinabove were used in the preparation of the novel compounds of generic formulae (I) and (II) according to the following Examples, which examples are illustrative only, and are not to be construed as limiting the scope of the invention.

EXAMPLE 1

4-(1,3-Dioxolan-2-yl)-2,6-dinitro-N,N-dipropylaniline

A mixture of 10 g. of 3,5-dinitro-4-(dipropylamino)-benzaldehyde, 20 ml. of 1,2-dihydroxyethane, 250 ml. of dry benzene, and 150 mg. of p-toluenesulfonic acid was stirred and refluxed, and a Dean-Stark trap was used to collect the evolved water of reaction. The reaction was continued for approximately 1 hour. At the end of that time, about 0.5 ml. of water had collected in the trap. The reaction product mixture was poured into about 500 ml. of sodium bicarbonate solution. The aqueous layer was separated and discarded and the organic layer was evaporated in vacuo to leave an orange oil. The orange oil was identified by infrared and NMR spectra as 4-(1,3-dioxolan-2-yl)-2,6-dinitro-N,N-dipropylaniline.

EXAMPLE 2

4-(4-Methyl-1,3-dioxolan-2-yl)-2,6-dinitro-N,N-dipropylaniline

A mixture of 3.0 g. of 3,5-dinitro-4-(dipropylamino)-benzaldehyde, 2.0 ml. of 1,2-propanediol, 75 ml. of benzene, and a small amount of p-toluenesulfonic acid was refluxed for about 4 hours, using a Dean-Stark trap to collect the evolved water. The reaction product mixture was cooled and extracted successively with saturated aqueous sodium bicarbonate solution, and brine, and then dried. The drying agent was filtered off and the benzene solution passed through an aluminum oxide column. The eluate was collected and evaporated. A total of 2.2 g. of 4-(4-methyl-1,3-dioxolan-2-yl)-2,6-dinitro-N,N-dipropylaniline was isolated as an oil.

EXAMPLE 3

4-(1,3-Dioxan-2-yl)-2,6-dinitro-N,N-dipropylaniline

A mixture of 4.0 g. of 4-(1,3-dioxan-2-yl)-2,6-dinitrochlorobenzene, 4.3 ml. of dipropylamine, and 100 ml. of benzene was stirred and refluxed for about 23 hours. The reaction product mixture was cooled and extracted with water and the organic layer separated and dried. The drying agent was filtered off. The organic layer, that is the benzene layer, was passed through aluminum oxide on a sintered glass funnel. The filtrate was evaporated to dryness and the residue was recrystallized from petroleum ether to yield a product having a melting point of about 61°–61.5° C. This product was identified by elemental analyses as 4-(1,3-dioxan-2-yl)-2,6-dinitro-N,N-dipropylaniline.

EXAMPLE 4

α,α-Dimethoxy-2,6-dinitro-N,N-dipropyl-p-toluidine

A mixture of 6 g. of 3,5-dinitro-4-(dipropylamino)-benzaldehyde, 100 ml. of methanol, and several drops of concentrated sulfuric acid was refluxed for about one hour. At the end of this time, 20 ml. of concentrated aqueous hydrochloric acid was added to the mixture and the mixture was refluxed for above five hours. The reaction product mixture was poured into a mixture of ice and water and the aqueous mixture was extracted with ethyl acetate. The ethyl acetate layer was washed successively with saturated aqueous sodium bicarbonate solution, saturated aqueous sodium chloride solution and then dried. The drying agent was filtered off. The ethyl acetate solvent was removed in vacuo to leave a residue which was recrystallized once from n-hexane and twice from methanol to yield product having a melting point of about 64°–66° C. The product was identified by elemental analyses as α,α-dimethoxy-2,6-dinitro-N,N-dipropyl-p-toluidine.

Following the same general procedure, and using appropriate starting materials, the following additional compound was prepared:

A. α,α-Diethoxy-2,6-dinitro-N,N-dipropyl-p-toluidine, as an oil.

EXAMPLE 5

4-(1,3-Dithiolan-2-yl)-2,6-dinitro-N,N-dipropylaniline

A mixture of 2.7 g. of 4-(1,3-dithiolan-2-yl)-2,6-dinitrochlorobenzene, 2.8 ml. of dipropylamine, and 75 ml. of benzene and refluxed for about 17 hours. The reaction product mixture was cooled and extracted with water, and the benzene layer separated and dried. The drying agent was filtered off and the benzene solution was passed through a small amount of aluminum oxide on a Buchner funnel. The filtrate was evaporated to dryness and the residue was recrystallized from ethanol to yield product having a melting point of about 89°–90.5° C. This product was identified by elemental analyses as 4-(1,3-dithiolan-2-yl)-2,6-dinitro-N,N-dipropylaniline.

EXAMPLE 6

2,6-Dinitro-4-(1,3-oxathiolan-2-yl)-N,N-dipropylaniline

A mixture of 2.0 g. of 3,5-dinitro-4-(dipropylamino)-benzaldehyde, 1.0 ml. of 2-mercaptoethanol, a small amount of p-toluenesulfonic acid, and 30 ml. of benzene was refluxed for about 1 hour, using a Dean-Stark trap to collect the evolved water of reaction. The reaction mixture was cooled and the reaction product mixture was extracted with saturated aqueous sodium bicarbonate solution, then with brine, and the benzene layer dried. The drying agent was filtered off and the benzene solution was passed through a small amount of aluminum oxide on a Buchner funnel. The filtrate was concentrated to remove the solvent and the residue obtained was recrystallized twice from ethanol to yield product having a melting point of about 47.5°–49° C. This product was identified by elemental analyses as 2,6-dinitro-4-(1,3-oxathiolan-2-yl)-N,N-dipropylaniline.

Following the same general procedure, the following additional compound was prepared.

A. 4-(m-Dithian-2-yl)-2,6-dinitro-N,N-dipropylaniline, having a melting point of about 111°–112° C.

The following experimental procedures were used to demonstrate the pre- and postemergent herbicidal efficacy of the novel compounds of this invention.

EXPERIMENT 1

A soil was prepared consisting of one part masonry sand and one part shredded topsoil blended together in a cement mixer. 1.65 liters of the masonry sand was placed in the bottom of a 25×35 cm. galvanized flat and leveled, and 2.9 liters of the above-identified soil and sand mixture was placed over the sand, leveled, and tamped with a bench brush. The crop seeds were planted in one-half the flat in individual rows made with a three-row marker, the rows being perpendicular to the long axis of the flat. Crop seeds consisting of four kernels of corn, five to eight cotton seeds, and five soybean seeds were placed in these rows. A four-band template was then placed on the remaining soil and about the indicated number of each of the following seeds were planted, one species to each section: 350 crabgrass (*Digitaria sanguinalis*); 40 mustard (*Brassica juncea*); 25 pigweed (*Amaranthus retroflexus*); and 40 foxtail millet (*Setaria italica*). The crabgrass was broadcast by hand, and the other seed sown with the help of a planting plate. There was then added to the flat one-half liter of soil to cover the entire flat. The weed seeds were covered to a depth of about 6 mm., and the crop plant seeds were covered to a depth of from about 2.5 to 3 cm. One pint of fertilizer solution containing 2.5 grams of a soluble fertilizer (18-25-18) was added to each flat after planting. The postemergent flats were fertilized immediately after planting and again prior to treatment. The preemergent flats were fertilized immediately after planting, only.

The postemergent flats were planted nine to twelve days prior to treatment with the herbicide test compounds, while the preemergent flats were planted the day prior to such treatment.

The compounds studied in this test were applied at 8 lb./acre pre- and postemergent. The formulation was accomplished by dissolving 120 mg. of the test compound in about 2.5 ml. of a relatively nonphytotoxic organic solvent such as ethanol or acetone. This solution was then diluted to a volumme of 25 ml., using an aqueous 0.2% solution of polyoxyethylene sorbitan monolaurate (Tween 20).

The herbicidal composition was applied to each flat with a modified DeVilbiss atomizer hooked to an air source. Twelve and one-half milliliters of the composition under test was applied to each flat, resulting in an application rate of 8 lb./200 gallons/acre. One pre- and one postemergent flat were treated at this rate for each compound. The preemergent flat was treated the day after planting, and the postemergent flat was treated nine to twelve days after planting. Injury ratings and observations were made from ten to thirteen days after treatment. The injury rating scale used was as follows:
1—no injury
2—slight injury
3—moderate injury
4—severe injury
5—death of plants Table 1, which follows, sets forth the results of the pre- and postemergent testing of a number of the novel compounds of this invention. In the table, column 1 identifies the compound by its operating example or preparation number; column 2, the rate in terms of pounds per acre at which the compound was applied to the test flat; and columns 3 to 14, the injury rating for the particular plant seedlings.

10-15 sugar beet seeds, 20-25 rice seeds, 80-100 mustard seeds (*Brassica juncea*), 40-50 jimsonweed seeds (*Datura stramonium*), and 60-75 smartweed seeds (*Polygonum pensylvanicum*). After planting, sufficient soil was added to cover the entire surface of each flat. The preemergent flats were planted the day prior to treatment and fertilized immediately after planting. The flats were fertilized by applying to each flat one pint of a fertilizer solution containing 2.5 grams of a soluble 23-19-17 fertilizer.

Each test compound was formulated by dissolving it in a mixture of Toximul R and S water and a mixture of acetone and ethanol (1:1) not to exceed 10% of the total volume in the spray solution. The Toximul R and S water contains Toximul R and Toximul S (sulfonate/nonionic blend) at concentrations of about 225 ppm. and 125 ppm. respectively. Those test compounds which Table 1

| | | Injury Rating on Pre- and Postemergent Treatment | | | | | | | | | | | | |
|---|---|---|---|---|---|---|---|---|---|---|---|---|---|---|
| | | Preemergent | | | | | | | Postemergent | | | | | |
| Compound | lb./A. | Corn | Cotton | Soybean | Crabgrass | Pigweed | Foxtail | Velvetleaf | Corn | Cotton | Soybean | Crabgrass | Pigweed | Foxtail | Velvetleaf |
| Ex. 2 | 8 | 1 | 1 | 1 | 4 | 4 | 4 | 3 | 1 | 2 | 3 | 3 | 3 | 3 | 2 |
| 3 | 8 | 1 | 1 | 1 | 4 | 2 | 4 | 2 | 1 | 1 | 1 | 1 | 1 | 1 | 1 |
| 4 | 8 | 1 | 1 | 1 | 4 | 4 | 5 | 3 | 3 | 1 | 3 | 4 | 4 | 4 | — |
| 4A | 8 | 1 | 1 | 1 | 4 | 4 | 4 | 3 | 1 | 1 | 1 | 3 | 2 | 1 | 2 |
| 5 | 8 | 1 | 1 | 1 | 3 | 3 | 3 | 2 | 1 | 1 | 2 | 1 | 3 | 1 | 2 |
| 6 | 8 | 1 | 1 | 2 | 4 | 4 | 4 | 3 | 1 | 2 | 2 | 3 | 3 | 2 | 2 |
| 6A | 8 | 1 | 1 | 1 | 2 | 2 | 1 | 1 | 1 | 1 | 2 | 1 | 1 | 1 | 1 |
| Prep. 3 | 8 | 1 | 1 | 1 | 3 | 3 | 3 | 1 | 1 | 2 | 1 | 1 | 1 | 1 | 1 |

EXPERIMENT 2

A second experiment was conducted to further study the preemergent activity of the novel compounds.

This second experiment utilized a total of fourteen species of plants, an additional seven species of plants over the number utilized in Experiment 1.

A soil was prepared consisting of one part masonry sand and one part shredded topsoil blended together in a cement mixer and placed in a 25×35 cm. galvanized flat. The soil was patted down with a bench brush until level. The flat contained bottom holes and grooves for drainage. The following quantities of seeds were planted in the flats thus prepared in rows perpendicular to the long axis of the flat: 100-150 large crabgrass seeds (*Digitaria sanguinalis*), 150-250 redroot pigweed seeds (*Amaranthus retroflexus*), 40-50 velvetleaf seeds (*Abutilon theophrasti*), 80-100 foxtail millet seeds (*Setaria italica*), 6 cottom seeds, 6 soybean seeds, and 4 seeds of corn. In a second flat there were planted the following test species: 6 cucumber seeds, 80-100 alfalfa seeds, were not soluble in the acetone-ethanol mixture were placed in Toximul R and S water and ground in a tissue grinder to form a suspension.

The formulated test compounds were applied to the soil surface the day after planting, using a modified DeVilbiss atomizer operating on an air line at a pressure of about 10 to 12 pounds per square inch pressure. Each flat received 12.5 ml. of the test solution, resulting in a spray volume of 200 gallons per acre. Injury ratings and observations as to type of injury were made eleven to thirteen days after treatment. The injury rating scale was the same as used in Experiment 1.

Table 2, which follows, sets forth the results of preemergent testing of the novel compounds of this invention, each of the test compounds being identified by its operating example number. In Table 2, column 1 gives the identity of the compound; column 2, the rate in terms of pounds per acre at which the compound was applied to the test flat; and columns 3 to 16, the injury rating for the particular plant seeds or seedlings.

Table 2

| Compound | lb./A. | Corn | Cotton | Soybean | Alfalfa | Sugarbeet | Rice | Cucumber | Crabgrass | Mustard | Pigweed | Foxtail | Velvetleaf | Jimsonweed | Smartweed |
|---|---|---|---|---|---|---|---|---|---|---|---|---|---|---|---|
| 1 | 8 | 2 | 1 | 1 | 4 | 3 | 3 | 1 | 4 | 2 | 5 | 4 | 3 | 1 | 3 |
| | 4 | 2 | 1 | 1 | 1 | 2 | 3 | 2 | 4 | 1 | 5 | 4 | 2 | 1 | 1 |
| | 2 | 2 | 1 | 1 | 1 | 1 | 1 | 1 | 4 | 1 | 5 | 4 | 3 | 1 | 1 |
| | 1 | 1 | 1 | 1 | 1 | 1 | 1 | 1 | 4 | 1 | 5 | 4 | 3 | 1 | 1 |
| | ½ | 1 | 1 | 1 | 1 | 1 | 1 | 1 | 4 | 1 | 3 | 4 | 1 | 1 | 1 |
| 2 | 4 | 1 | 1 | 1 | 2 | 2 | 2 | 1 | 4 | 1 | 3 | 2 | 3 | 1 | — |
| | 2 | 1 | 1 | 1 | 1 | 1 | 2 | 1 | 4 | 1 | 3 | 3 | 2 | 1 | — |
| | 1 | 1 | 1 | 1 | 1 | 1 | 1 | 1 | 3 | 2 | 2 | 2 | 1 | 1 | — |
| 3 | 4 | 1 | 1 | 1 | 2 | 1 | 3 | 2 | 4 | 1 | 3 | 3 | 2 | 1 | — |
| | 2 | 1 | 1 | 1 | 2 | 1 | 3 | 1 | 3 | 1 | 3 | 2 | 1 | 1 | — |
| | 1 | 1 | 1 | 1 | 1 | 1 | 1 | 1 | 1 | 1 | 1 | 1 | 1 | 1 | — |
| 4 | 4 | 1 | 1 | — | 3 | 2 | 2 | 1 | 5 | 2 | 3 | 4 | 2 | — | — |
| | 2 | 1 | 1 | — | 2 | 1 | 1 | 1 | 5 | 1 | 3 | 4 | 2 | — | — |
| | 1 | 1 | 1 | — | 1 | 1 | 1 | 1 | 4 | 1 | 3 | 4 | 1 | — | — |
| 4A | 4 | 1 | 1 | 2 | 2 | 3 | 2 | 1 | 4 | 2 | 3 | 4 | 1 | 1 | — |

Table 2-continued

| Compound | lb./A. | Corn | Cotton | Soybean | Alfalfa | Sugarbeet | Rice | Cucumber | Crabgrass | Mustard | Pigweed | Foxtail | Velvetleaf | Jimsonweed | Smartweed |
|---|---|---|---|---|---|---|---|---|---|---|---|---|---|---|---|
| | 2 | 1 | 1 | 1 | 3 | 2 | 1 | 1 | 4 | 1 | 2 | 4 | 1 | 1 | — |
| | 1 | 1 | 1 | 1 | 1 | 1 | 1 | 1 | 4 | 1 | 2 | 2 | 1 | 1 | — |
| 6 | 4 | 1 | 1 | 1 | 1 | 1 | 2 | 1 | 3 | 1 | 2 | 3 | 1 | 1 | — |
| | 2 | 1 | 1 | 1 | 1 | 1 | 1 | 1 | 3 | 1 | 1 | 3 | 1 | 1 | — |
| | 1 | 1 | 1 | 1 | 1 | 1 | 1 | 1 | 1 | 1 | 1 | 1 | 1 | 1 | — |

As is well understood in the art, the rates of application of herbicide required to produce a given reult under the carefully controlled conditions of the greenhouse are usually less than those required in the field.

I claim:

1. A compound of the formula

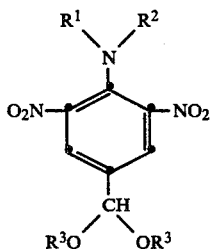

wherein
$R^1$ represents
(A) $C_1$–$C_6$ alkyl, optionally monosubstituted with
  (1) methoxy,
  (2) halo,
(B) $C_3$–$C_4$ alkenyl,
(C) halo($C_3$–$C_4$)alkenyl,
(D) $C_3$–$C_4$ alkynyl, or
(E) cyclopropylmethyl;
$R^2$ represents
(A) $C_1$–$C_6$ alkyl, optionally monosubstituted with
  (1) methoxy,
  (2) halo,
(B) $C_3$–$C_4$ alkenyl,
(C) halo($C_3$–$C_4$)aikenyl,
(D) $C_3$–$C_4$ alkynyl, or
(E) cyclopropylmethyl;
(F) hydrogen;
provided that $R^1$ and $R^2$ together contain no more than 8 carbon atoms; and $R^3$ is $C_1$–$C_3$ alkyl.

2. The compound as in claim 1, said compound being α,α-dimethoxy-2,6-dinitro-N,N-dipropyl-p-toluidine.

3. The compound as in claim 1, said compound being α,α-diethoxy-2,6-dinitro-N,N-dipropyl-p-toluidine.

4. A method for inhibiting the growth of unwanted vegetation which comprises applying to a locus of said vegetation an herbicidally-effective amount of a compound of claim 1.

5. The method of claim 4 wherein said compound is applied in combination with an inert diluent.

6. The method of claim 4 wherein said compound is applied in combination with a surfactant and an inert diluent.

7. The method of claim 4 wherein said compound is applied at a rate between about ½ and about 32 pounds per acre.

8. The method of claim 4 wherein α,α-dimethoxy-2,6-dinitro-N,N-dipropyl-p-toluidine is the herbicidal compound.

9. The method of claim 4 wherein α,α-diethoxy-2,6-dinitro-N,N-dipropyl-p-toluidine is the herbicidal compound.

* * * * *